(12) United States Patent
Fehr

(10) Patent No.: US 9,925,397 B2
(45) Date of Patent: *Mar. 27, 2018

(54) CONDITIONING COMPOSITION

(75) Inventor: Daniel Fehr, Zurich (CH)

(73) Assignee: Straumann Holding AG, Basel (CH)

( * ) Notice: Subject to any disclaimer, the term of this patent is extended or adjusted under 35 U.S.C. 154(b) by 322 days.

This patent is subject to a terminal disclaimer.

(21) Appl. No.: 13/114,687

(22) Filed: May 24, 2011

(65) Prior Publication Data

US 2011/0301240 A1  Dec. 8, 2011

(30) Foreign Application Priority Data

Jun. 3, 2010 (EP) ..................................... 10164851

(51) Int. Cl.
*A61K 31/198* (2006.01)
*A61Q 11/00* (2006.01)
*A61K 8/44* (2006.01)
*A61Q 11/02* (2006.01)

(52) U.S. Cl.
CPC ............... *A61Q 11/00* (2013.01); *A61K 8/44* (2013.01); *A61Q 11/02* (2013.01); *A61K 2800/88* (2013.01)

(58) Field of Classification Search
CPC ................................ A61K 31/198; A61K 8/44
USPC ........................ 514/566; 424/78.38
See application file for complete search history.

(56) References Cited

U.S. PATENT DOCUMENTS

| 3,988,434 | A | | 10/1976 | Schole et al. | |
|---|---|---|---|---|---|
| 4,554,050 | A | * | 11/1985 | Minford et al. | ............. 216/108 |
| 4,850,872 | A | | 7/1989 | Goldman et al. | |
| 5,122,365 | A | * | 6/1992 | Murayama | ...................... 424/49 |
| 2004/0191188 | A1 | | 9/2004 | Freedman | |
| 2006/0069186 | A1 | | 3/2006 | Smigel | |

FOREIGN PATENT DOCUMENTS

| DE | 4028947 A1 | 3/1992 |
|---|---|---|
| EP | 0079611 A2 | 5/1983 |
| EP | 1557180 A1 | 7/2005 |
| WO | WO 86/03674 A1 | 7/1986 |
| WO | WO 96/09029 A1 | 3/1996 |
| WO | WO 2009/083281 A1 | 7/2009 |

OTHER PUBLICATIONS

Ari et al. "Effects of endodontic irrigation solutions on mineral content of root canal dentin using ICP-AES technique" 2005, vol. 31, Issue 3, pp. 187-189.*
Lowenguth RA, Blieden TM, Periodontal regeneration: root surface demineralization, Periodontology 2000, 1993; 1:54.

* cited by examiner

*Primary Examiner* — Jennifer M Kim
(74) *Attorney, Agent, or Firm* — Polsinelli PC

(57) ABSTRACT

The present invention is directed to a composition for the conditioning of a dental mineralized surface and/or a dental implant and/or for increasing the hydrophilicity of a dental implant having a metal containing surface. The composition comprises EDTA in a concentration of 21-55% by weight and having a pH of 9.0 or above. The high pH of the composition allows more EDTA to be dissolved and the composition is useful for the conditioning of mineralized dental surfaces and/or surfaces of dental implants. The composition of the invention may thus be used for the conditioning of mineralized dental surfaces and dental implant surfaces in order to remove e.g. biofilm, debris, bacteria, bacterial toxins etc and/or for increasing the hydrophilicity of an implant having a metallic surface. The invention is also directed to a kit comprising the composition of the invention and a device to apply the composition to a surface in need of conditioning.

18 Claims, 1 Drawing Sheet

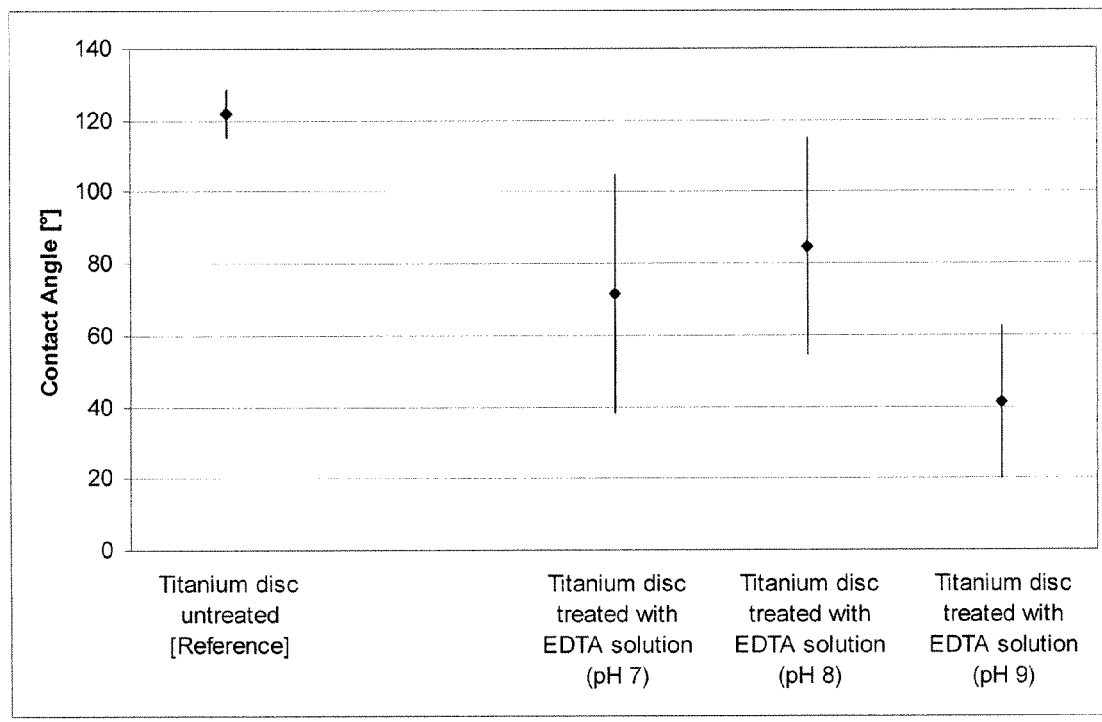

CONDITIONING COMPOSITION

This application claims the benefit of priority to European Patent Application No. 10164851.7 filed on Jun. 3, 2010.

TECHNICAL FIELD

The present invention is within the field of compositions for conditioning of mineralized dental surfaces and/or dental implant surfaces. In particular, the invention is directed to a composition comprising EDTA to be used for the removal of e.g. biofilm, bacteria, debris, bacterial toxins, tissue etc. from a dental surface and/or a dental implant surface and/or for increasing the hydrophilicity of a dental implant having a metallic surface. More particularly, the invention is directed to the composition for use in treating disease such as periodontal disease, periimplantitis, caries and/or an infection and/or inflammation in the root canal.

BACKGROUND ART

Diseases affecting the oral cavity and the teeth and their supporting tissue are very common in adult humans. Such diseases can have a large impact on the individuals affected as they may cause pain, problems with chewing, tooth loss, bad breath etc. and even affect the whole body due to inflammations causing systemic immune responses.

Periodontal disease is an oral disease affecting almost all adults. It is a progressive disease having the serious consequence of leading to partial or complete tooth loss. Periodontal diseases affect the tissues that support and anchor the teeth. The tissues affected by periodontal disease are the gums (including the gingival) periodontal ligament, cementum, and alveolar bone. If not treated, periodontal disease results in the destruction of the gums, alveolar bone, and the outer layer of the tooth root. The main area involved in periodontal disease is the gingival sulcus, a pocket between the teeth and the gums.

Periodontal disease may occur in different forms: gingivitis, acute necrotizing ulcerative gingivitis, adult periodontitis, and localized juvenile periodontitis.

Gingivitis is an inflammation of the outermost soft tissue of the gums which become red and inflamed, loose their normal shape, and becomes prone to bleeding.

Periodontitis is a condition in which gingivitis has extended down around the tooth and into the supporting bone structure. Anaerobic bacteria may grow in pockets between the gums and teeth formed by the accumulation of plaque and tarter. When the bacteria reach the roots of the teeth, the bacteria further cause damage to the tooth supporting bone structure.

Adult periodontitis is the most serious form of the periodontal diseases. It involves the gingiva, periodontal ligament, and alveolar bone, resulting in deep periodontal pockets forming between the teeth, the cementum, and the gums. Plaque, calculus, and debris from food and other sources collect in the pocket. If left untreated, the periodontal ligament can be destroyed and resorption of the alveolar bone may occur allowing the teeth to move more freely and eventually be lost.

The risk of being afflicted by periodontal disease increases with age and bad oral hygiene. The presence of certain species of bacteria in large enough numbers in the gingival pocket and related areas correlates with the development of periodontal disease; removal of these bacteria correlates with reduction or elimination of disease.

Periodontal disease can usually be prevented by good dental hygiene, such as by tooth brushing and flossing. However, once tartar is formed, it has to be removed by a dentist. Also, treatment of periodontitis requires professional dental care. The pockets around the teeth must be cleaned, and all tartar and plaque removed, all the way down to the root if this is also afflicted. Conventional treatment involves both surgical and non-surgical procedures. Surgery may in particular be necessary where the pockets are very deep. Also, antibiotic treatment to remove infectious bacteria may be necessary.

Normally, treatment starts by scraping (scaling and root planing) the tooth surfaces in order to remove both visible bacterial deposits and dental calculus and deposits hidden below the gingival margin. This reduces gingival swelling caused by inflammation and often reduces the depth of the periodontal pockets. However, adequate scaling and root planing performed below the gingival margin is difficult and in deeper periodontal pockets inaccessible infected sites will serve as reservoirs for reinfection. Consequently, surgical procedures, which will enhance access and visibility, may have to be used to completely eliminate soft and hard bacterial deposits. During periodontal surgery, the periodontitis-affected roots are exposed by detaching the gingiva from the roots and alveolar bone. The roots are then freed from bacterial deposits and dental calculus by scaling and root planing. This involves also removal of granulation tissue and root cementum contaminated by bacterial toxins. After the area has been cleaned, the gingival flaps are repositioned and sutured.

Such conventional treatment procedures are conservative and will only, at best, preserve the remaining tooth supporting tissues. Thus, tooth support that has already been lost cannot be recreated by conventional treatment.

Periodontal healing is a primary concern in the treatment of periodontal disease. This is a process largely dependent on the tissue reactions taking place at the hard/soft tissue interface on the root surface. Long-term studies on healing of periodontal wounds with marginal communication following periodontal treatment have indicated that cellular colonization of the wounded area results from a competition between alveolar bone, oral epithelium and mucosal connective tissue as well as periodontal connective tissue.

Most often deep furcation involvements do not lend themselves to successful periodontal healing with conventional periodontal surgery.

Etching during periodontal surgery is performed mainly with three aims: removal of bacterial toxins, removal of smear layer and exposure of collagenous fibres in the root surface and increase visibility through hemostatic effects.

Of these, the two first have been evaluated in vitro employing mainly citric acid and to some extent orthophosphoric acid both of which operate at a pH of around 1 (Lowenguth R A, Blieden T M. Periodontal regeneration: root surface demineralization. Periodontology 2000 1993; 1:54).

Scaling and root planing is performed to remove bacterial deposits, calculus and the superficial layers of the root surface (cementum and dentin), structures and tissues which harbor bacterial toxins. Such toxins are not only confined to the bacterial deposits but are also found adsorbed to periodontally diseased root surfaces.

These substances have been shown to inhibit cell attachment in vitro, a function necessary for healing. Thus, the aim of scaling and root planing is to provide a biologically acceptable surface for marginal healing. However, following root surface instrumentation, areas of contaminated cementum, as well as a smear layer covering the instrumented surfaces may still remain. Additional root surface treatment, such as etching has been reported to remove the smear layer.

Application of etching agents has been reported to remove smear and debris which may result from scaling and root planing. However, it also affects the mineralized root surface, although contradictory results have been reported depending on mode of application of the agent.

Burnishing the root surface with a cotton pellet soaked in citric acid appears to expose more intertubular fibrils and widen dentinal tubules to a greater extent compared to simple application of a drop of the acid or by placing an acid-saturated cotton pellet on the root surface without rubbing, although reports have also indicated no difference.

Several studies have studied periodontal healing following citric or ortho-phosphoric acid etching of root surfaces exposed during periodontal surgery, while only few studies have evaluated surrounding soft tissue reactions after acid application. A surprisingly small area of the soft tissue around the site of application appears to suffer any damage despite the low pH (around 1). However, more profound effects on periodontal healing have been reported, although the results appear highly variable.

Since its inception citric and ortho-phosphoric acid etching (pH 1) of root surfaces have been reported to result in new attachment or reattachment. Later these claims have been disputed, and most in vivo studies indicate that connective tissue healing with some reparative cementum formation will result rather than formation of a long epithelial junction. There is also reason to believe that application of citric or ortho-phosphoric acid to a periodontal wound during surgery will increase visibility through hemostatic effects as well as facilitate removal of granulation tissue.

WO96/09029 discloses a composition comprising EDTA for use for conditioning of a biological mineralized surface. The amount of EDTA of the composition of WO96/09029 is near or at saturation of the EDTA when in an aqueous matrix, the saturation point for EDTA lying between 22 and 27% by weight based on the water content of the composition. The pH of the composition is from 6 to 8, preferably around neutral pH of 7. This composition was demonstrated to selectively remove hydroxyapatite but not the collagenous matrix of dentin, in contrast to ortho-phosphoric acid-based etching compositions.

Restorative materials are widely used in the medical field. In the dental area, restorative materials such as amalgam or resin composites are often used to repair dental tissues and bones, for example in the case of dental caries or restoration of tooth injuries. However, in order for such materials to be able to firmly attach to the tooth, the surface of the tooth has to be clean and without adhering bacteria, calculus etc. Also in the case of root fillings, the tooth root canal has to be cleaned and the pulp removed therefrom.

Dental implants are utilized in dental restoration procedures in patients having lost one or more of their teeth. A dental implant comprises a dental fixture, which is utilized as an artificial tooth root replacement. Thus, the dental fixture serves as a root for a new tooth. The dental fixture is typically a screw, i.e. it has the shape of a screw, and it is typically made of titanium, a titanium alloy, zirconium or a zirconium alloy. The screw is surgically implanted into the jawbone, whereafter the bone tissue grows around the screw and the screw is fixated in the bone with the bone in close contact with the implant surface. This process is called osseointegration, because osteoblasts grow on and into the surface of the implanted screw. By means of the osseointegration, a rigid installation of the screw is obtained.

Once the implant screw is firmly anchored in the jawbone, it may be elongated by attachment of an abutment to the screw. The abutment may, just as the screw, be made of titanium, a titanium alloy, zirconium or a zirconium alloy. The shape and size of the utilized abutment are adjusted such that it precisely reaches up through the mucosa after attachment to the screw. A dental restoration such as a crown, bridge or denture may then be attached to the abutment.

Alternatively, the implant screw has such a shape and size that it reaches up through the mucosa after implantation, whereby no abutment is needed and a dental restoration such as a crown, bridge or denture may be attached directly to the screw.

The surface of dental implants sometimes has to be cleaned after placing. This is particularly important when an infection or contamination occurs, causing a progressive degenerative process in the bone adjacent to the implant known as periimplantitis. This is an inflammatory condition of the mucosa and/or bone around the implant which may result in bone loss and eventual loss of the implant. Currently there is no universal agreement on the best treatment for peri-implantitis. However, in periimplantitis it is important to clean the surface of the ailing implant from microbes and contaminants to stop the progression of the disease and ensure re-integration of the implant. Failure to clean the implant surface will eventually lead to loss of bone and implant, and make further alternative treatments difficult and sometimes even impossible. This cleaning may involve mechanical as well as chemical treatment of the implant and the surrounding bone and tissue.

In conclusion, it is important in many aspects to be able to efficiently clean the surface of a mineralized tissue or an implant. Also, there is a need for a composition allowing the cleaning of an implant surface in order to enhance and/or enable osseointegration of the implant. Also, there is a need for a conditioning composition allowing for the treatment of periimplantitis. Thus there is still a need in the field for efficient compositions allowing for a sufficient conditioning of the surface of a mineralized tissue or a medical implant in order to prevent and/or treat diseases affecting the oral cavity, such as periodontal disease and periimplantitis.

SUMMARY OF INVENTION

The object of the present invention is to provide compositions for the conditioning of mineralized dental surfaces and/or surfaces of dental implants and/or for increasing the hydrophilicity of a dental implant having a metal containing surface.

This object is achieved by the provision of a conditioning composition comprising ethylenediaminetetraacetic acid (EDTA) at a concentration in the range of 21-55% by weight and having a pH of at least 9.0.

Due to the high pH of the conditioning composition of the invention, it was found that a higher amount of EDTA is dissolved than is possible when a lower pH is used. Thereby EDTA may be dissolved at a higher degree compared to its normal saturation point in compositions having a pH around neutral, even if the compositions contain the same total amount of EDTA. The conditioning composition is more effective in the conditioning of mineralized dental surfaces and/or surfaces of dental implants. For example biofilm dissolution is increased. Also the hydrophilicity of a surface of an implant having a metal containing surface is significantly increased when the conditioning composition of the invention is used for conditioning the surface of the implant. A high hydrophilicity of an implant surface is desirable e.g.

as this has the effect of accelerating bone and soft tissue regrowth on and around the implant. When an implant surface is conditioned with a composition of the invention the osseointegration of the implant may be enabled and/or enhanced. Also, the use of the composition of the invention has advantageous effects in the case of periimplantitis.

The present invention is therefore also directed to the use of a conditioning composition for the conditioning of a mineralized dental surface and/or a surface of a dental implant and/or for improving the hydrophilicity of an implant having a metal containing surface.

The invention is further directed to the conditioning composition for use as a medicament, such as for use in the treatment of a periodontal disease, periimplantitis, caries and/or an infection and/or inflammation in the root canal.

The invention is also directed to a kit comprising a vial with the conditioning composition and a device for the conditioning of a mineralized dental surface and/or a surface of a dental implant.

Definitions

By "weight %", "% by weight", "wt %" and the like is in the present context meant the amount of a solute (by weight) in a solution based on the total weight of the solution, i.e. to be calculated by the formula: (grams solute/grams solution)×100. This means that e.g. a composition comprising 21 g of EDTA in 79 g of water comprises 21 wt % of EDTA.

By "conditioning" is in the present context meant the cleaning of a surface, such as a mineralized surface or the surface of an implant having a metal containing surface, in order to remove e.g. biofilm, bacterial toxins, debris, bacteria, dental calculus (mineralized bacterial deposits) and/or tissue remnants. Conditioning of a tooth surface also includes the removal of hydroxyapatite to expose collagen on the tooth root. "Conditioning" may thus be seen as a cleaning of a surface to remove unwanted substances therefrom and/or prepare the treated surface in order to enable and/or support the regeneration of the surrounding tissue onto the conditioned surface. The conditioning of a surface using the composition of the invention may also include an etching of said surface.

By "an implant having a metal containing surface" and the like is in the present context meant an implant whose surface in part or fully contains a metal material. For example approximately 10, 20, 30, 40, 50, 60, 70, 80, 90 or 100% of the surface may be made of metal. The structure underlying the implant surface may be made of a metal material or another material, such as a ceramic or polyethylene. The metal material may e.g. be titanium or a titanium alloy, chromium or a chromium alloy, zirconium or a zirconium alloy, aluminium or an aluminium alloy, tantalum or stainless steel.

DETAILED DESCRIPTION OF INVENTION

Figure 1:
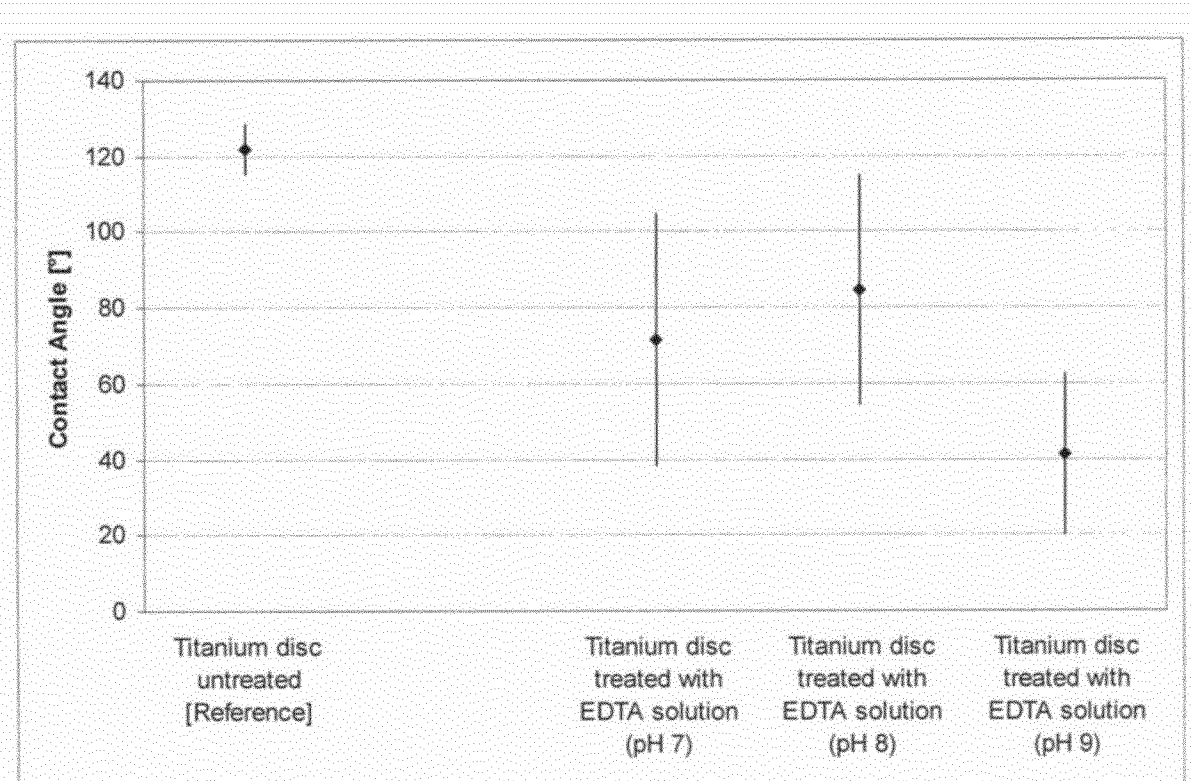
FIG. 1 shows the contact angles of titanium discs treated with EDTA compositions having different pH.

The present invention is directed to a composition comprising ethylenediaminetetraacetic acid (EDTA) at a concentration in the range of about 21-55% by weight and having a pH of at least 9.0. Such a composition is advantageous for the conditioning of mineralized dental surfaces and/or surfaces of a dental implant and/or for increasing the hydrophilicity of an implant having a metal containing surface. Suitable sources for EDTA include but are not limited to EDTA with one or more acid groups carrying monovalent metal ions, such as, but not limited to, $Na^+$ or $K^+$. Examples of such sources include, but are not limited to disodium EDTA, tetrasodium EDTA and ethylenedinitril tetraacetic acid. Preferably the monovalent metal ion is $Na^+$.

The present inventors have surprisingly found that it is possible to prepare a composition comprising a higher concentration of dissolved EDTA by raising the pH of the composition. Due to the raise in pH to 9.0 or above, it was found possible to dissolve EDTA above its normal saturation point in aqueous solutions. As a comparison, in the composition of WO96/09029, due to the lower pH of that composition, not all of the EDTA added is dissolved but some remains undissolved, even if the total amount of EDTA is the same as the amount of EDTA in the composition of the present invention. As is demonstrated in the experimental section (Example 2) the solubility of EDTA is greatly enhanced with a pH of 9. The composition is totally clear with a pH of 9. However, the composition is not completely clear at pH 8 and at pH 7. At pH 7, the solubility of the EDTA is in the order of about 10-12%. Thus one advantage of the use of a higher pH is that EDTA is available in a much higher concentration to a surface to be treated with the composition. The combination of a high pH of the solution and the high concentration may be particularly advantageous to increase the hydrophilicity of a titanium surface. Also, by the use of a high pH, the negative effect on bone regeneration that may be caused by the use of conditioning compositions having a low pH may be decreased.

The present composition was found have advantageous effects when used for the conditioning of a mineralized dental surface and/or the surface of a dental implant. For example biofilm dissolution was increased. Also it was surprisingly found that the hydrophilicity of a metallic implant surface was increased when the conditioning composition of the invention was used for conditioning of an implant surface. A high hydrophilicity of an implant surface is desirable e.g. as this has the effect of accelerating bone and soft tissue regrowth on and around the implant. Conditioning an implant surface with the composition of the invention may thus have the effect of enabling and/or enhancing the osseointegration of the implant.

The present invention therefore encompasses a composition comprising ethylenediaminetetraacetic acid (EDTA) at a concentration in the range of 21-55% by weight and having a pH of at least 9.0. Due to its advantageous effect on conditioning of mineralized surfaces and/or surfaces of an implant, the composition may also be denoted a "conditioning composition".

EDTA is an agent which chelates divalent cations, such as $Ca^{2+}$, $Mg^{2+}$, $Fe^2$ and $Pb^{2+}$. It is widely used in infusion solutions for detoxification and as an anticoagulant in vivo. In vitro it has a variety of uses such as to detach cells from solid substrates, decalcification of tissue specimens before sectioning and staining and as a detergent in biochemical analysis.

Etching of dentin or enamel is often performed as a surface treatment in connection with bonding a composite resin to dentin or enamel with a bonding agent or when binding a metal or orthodontic bracket to dentin or enamel of tooth. With conventional etching agents operating at a low pH, such as pH 1, not only the mineral component of exposed dentin surfaces is dissolved, but also the collagenous matrix. Collagen is dissolved at acid pH by acids such as citric acid already at weak concentrations. In WO96/

09029 it was demonstrated that EDTA etching in contrast to conventional etching agents will selectively remove hydroxyapatite but not the collagenous matrix of dentin.

The range of the pH of a composition of the invention may e.g. be about 9.0-11.5, such as 9.0-10.5. The pH of the composition may thus be e.g. 9.0, about 9.5, about 10.0, about 10.5, about 11.0 or about 11.5. It may be preferable to use a pH of 9.0-10.0 as such a pH has a less risk of damaging tissue while still providing a sufficiently high amount of EDTA to be dissolved. The pH may e.g. be adjusted by the use of any base (i.e. a pH buffering agent) suitable for the intended use of the composition, such as ammonia and hydroxides of alkali metals and alkaline earth metals. Examples include, but are not limited to NaOH, KOH, LiOH, CsOH, RbOH and non-metallic bases such as tri-ethanolamine (Trolamine), diethanolamine, ethanolamine, $NH_3$, phosphates such as $Na_2HPO_4$, $Na_3PO_4$, carbonates ($Na_2CO_3$), and bicarbonate ($NaHCO_3$).

The concentration of EDTA may e.g. be in the range of about 21-55% by weight, for example about 21-27, 21.6-26.4, 26-30, 30-35, 35-40, or 40-50% by weight. For example, the concentration of EDTA may be about 21.6, 22.0, 22.5, 23.0, 23.5, 24.0, 24.5, 25.0, 25.5, 26.0, 26.4, 27, 28, 29, 30, 35, 40, 45, 50, or 55% by weight.

A composition of the invention having an amount of EDTA of about 21-27% by weight (with a pH as specified herein) enable a substantial part or all of the EDTA to be dissolved in the solution, thereby providing a composition which contains no or little undissolved EDTA.

If the EDTA is provided at a higher concentration, such as e.g. about 40-50% by weight, some EDTA remains undissolved. This undissolved EDTA may provide an additional abrasive effect to the composition, in particular when used in combination with a cleaning tool, such as the tool described in WO2009083281. For example, plaque may be more easily removed in this way. Such a composition having both a high concentration of EDTA (e.g. 40-50% by weight) and a pH above 9 has both the advantageous properties of a high amount of dissolved EDTA and an additional amount of undissolved EDTA being able to provide an abrasive effect.

A composition of the invention may also contain a viscosity increasing agent (viscosity modifier). The composition may thus e.g. take the form of a gel or a semi-fluid material. The use of such a viscosity increasing agent allows a composition of the invention to be applied to a particular site and then essentially stay in place there. Thereby the composition is less likely to "spill", or drip onto an undesired surface, for example a tissue not subject to the treatment, such as the tongue, gums or pallet. This may be advantageous as the composition of the invention is a powerful conditioning composition, in particular considering the high pH of the composition and the high concentration of EDTA, which may harm sensitive tissue if not handled with care. By the use of a viscosity increasing agent, it is possible to apply the composition in one place and reduce the risk that the composition reaches surrounding tissue.

The amount of viscosity-increasing agent is typically maximally around 15% by weight. It may be advantageous to use a lower concentration of viscosity modifier in order to reduce the risk for negative interference of the viscosity modifier with the surface to be conditioned or the EDTA. Preferably the amount of viscosity modifier is about 1 to 5% by weight, e.g. about 1-5, 2.5-5.5, 3-5, 4-5% by weight. The amount of viscosity increasing agent may thus be e.g. about 1.0, 1.5, 2.0, 2.5, 3.0, 3.5, 4.0, 4.5, or 5.0.

The viscosity increasing agent may e.g. be selected from biocompatible polysaccharides, proteins, glycoproteins and synthetic polymers. For example, the viscosity increasing agent may be selected from celluloses and derivatives and/or salts thereof, starches and derivatives and/or salts thereof, plant gums, capsular microbial polysaccharides, and algal polysaccharides. Suitable salts of these include any salt that is pharmaceutically acceptable, such as sodium salts.

Examples of suitable derivatives of cellulose include, but are not limited to ethylcellulose, a water-insoluble commercial thermoplastic used in coatings, inks, binders, and controlled-release drug tablets; methylcellulose; hydroxypropyl cellulose; carboxymethyl cellulose; hydroxypropyl methyl cellulose, E464, commonly used as a viscosity modifier, gelling agent, foaming agent or binding agent; hydroxyethyl methyl cellulose, which is used in production of cellulose films.

Examples of derivatives of starch (modified starch) suitable for the present invention include, but are not limited to modified food starches which are starches that has been chemically modified to allow the starch to function properly under conditions frequently encountered during processing or storage, such as high heat, high shear, low pH, freeze/thaw and cooling.

A particularly interesting viscosity increasing agent for the purposes of the present invention is carboxymethylcellulose (CMC), or a salt thereof, such as the sodium salt of carboxymethylcellulose. CMC is preferred as it is previously safely used in other medical devices, it is relatively heat resistant, pseudoplastic and available in different modifications and/or viscosity ranges.

The composition of the invention is preferably formulated as an aqueous composition, i.e. water is used as a solvent to dissolve the EDTA. The amount of water in the composition is preferably at least 65% by weight, i.e. the water content of the composition is about 65-79 wt %, such as about 65, 66, 67, 68, 69, 70, 71, 72, 73, 74, 75, 76, 77, 78 or 79 wt %, in particular 70-79 wt %, unless a concentration of EDTA of 35% by weight or more is used, in which case the amount of water naturally has to be decreased. The water is preferably water for injection.

The composition of the invention may also consist of the EDTA in an amount as specified herein, a pH buffering agent, an aqueous solvent and optionally a viscosity increasing agent, wherein the composition has a pH as specified herein. One example of such a composition is composition consisting of EDTA at a concentration in the range of 21.6-26.4 by weight, a pH buffering agent in an amount so that the pH of the composition is 9.0-10.5, an aqueous solvent, and optionally a viscosity increasing agent, such as carboxymethylcellulose. Another example is a composition consisting of EDTA at a concentration in the range of about 21.6-26.4 by weight, a pH buffering agent in an amount so that the pH of the composition is pH of about 9.0-10.0, an aqueous solvent, and optionally a viscosity increasing agent, such as carboxymethylcellulose. Yet another example is a composition consisting of EDTA at a concentration in the range of about 21.6-26.4 by weight, a pH buffering agent in an amount so that the pH of the composition is ca 9.5, an aqueous solvent, and optionally a viscosity increasing agent, such as carboxymethylcellulose. One example of a composition of the invention having a higher amount of EDTA is a composition consisting of EDTA in the range of about 40-50% by weight, a pH buffering agent in an amount so that the pH of the composition is about 9.5 or above, an aqueous solvent and a viscosity increasing agent. Examples of suitable pH buffering agents and viscosity increasing agents are described elsewhere herein.

Optionally, the composition of the invention does not contain any NaOCl.

The composition of the invention may be used for the conditioning of a mineralized dental surface and/or a surface of a dental implant, preferably a dental implant having a metal containing surface. The invention therefore also is directed to the use of the composition for the conditioning of a mineralized dental surface and/or a surface of a dental implant. The conditioning may take place in situ in a subject, such as a human subject, or may take place ex situ, i.e. the conditioning takes place outside the body. The composition may thus be used for in situ conditioning and/or for ex situ conditioning. One aspect of the invention is thus directed to the use of the composition for the conditioning of a mineralized dental surface and/or a surface of a dental implant, wherein said conditioning takes place ex situ. For example, an implant may be conditioned before implantation in a body. An implant or a loose tooth may also be removed from the body, conditioned and then repositioned in the body.

Examples of mineralized dental surfaces which may be conditioned with the composition of the invention include, but are not limited to, bone in the oral cavity, such as alveolar bone, and tooth surfaces. Examples of mineralized dental surfaces thus include dentin and enamel. A tooth is composed of the crown, which is the area covered in enamel above the cementoenamel junction and the root, which is found below the cementoenamel junction and is covered with cementum. The crown is mainly composed of dentin with the pulp chamber in the center. Dentin also composes most of the root, which normally have pulp canals. A root canal is the space within the root of a tooth and contains the pulp chamber, the main canal(s), and more intricate anatomical branches that may connect the root canals to each other or to the surface of the root. The pulp can be damaged e.g. by decay, injury and/or gum disease. Such damage may lead to an infection in the tooth causing blood vessels and nerves to die, eventually leaving the tooth "dead". Root canal treatment may be used to remove damaged pulp and infections bacteria. The empty root canal system is then cleaned, filled and a permanent seal is put over the top of the tooth. In order for such a root filling to be successful, it is important that the dead and/or infected tissue, including any bacteria, is efficiently removed before filling the root canal. The composition of the invention is very suitable for such treatment of root canals and the mineralized dental surface to be conditioned with a composition of the invention may thus in different embodiments of the invention preferably be a root canal surface.

Implant surfaces to be conditioned with a composition of the invention may be any kind of implant surfaces, such as the surface of a metallic, ceramic or plastic implant. The composition of the invention is particularly suitable for the conditioning of dental implants having a metal containing surface. In different embodiments of the invention, the surface conditioned is thus the surface of a dental implant having a metal containing surface. As explained above, not the entire surface of the implant or the entire underlying structure has to be made of metal, but any metal containing parts of the surface may benefit from the conditioning by use of the composition of the invention. The conditioning may either be performed in situ i.e. when the implant is in place in a body or it may be performed before implantation. Alternatively, an implant (e.g. a crown) may be removed from a body, cleaned and repositioned in a body, i.e. the conditioning takes place ex situ. The conditioning of an implant having a metal containing surface using the composition of the invention has, in addition to the cleaning activity of the composition removing unwanted substances (such as biofilm) as explained later, the additional advantage of improving the hydrophilicity of the implant. A high hydrophilicity of an implant surface is desirable e.g. as this has the effect of accelerating bone and soft tissue regrowth on and around the implant. The composition of the invention may thus also be used to improve the hydrophilicity of an implant, before implantation of a new implant and/or during the cleaning (conditioning) of an implant removed from a body before its repositioning therein. One aspect of the invention is therefore directed to the use of a composition of the invention for improving the hydrophilicity of a dental implant, such as a dental implant having a metal containing surface.

Restorative materials which benefit from conditioning by the composition of the invention include those known in the art. Composite materials, synthetic bone materials, bone-like apatite and hydroxyapatite materials are well suited for use with the compositions and methods of the invention. Suitable examples of dental restoratives include composite filling materials, inlays, onlays, crown, bridges, ceramics, veneers and Maryland bridges. As mentioned above, the composition of the invention may also be used to prepare a clean mineralized surface before the application of a restorative material thereto.

The effective removal of biofilm, bacterial toxins, debris, bacteria, dental calculus (mineralized bacterial deposits) and/or tissue remnants by the conditioning effect of the composition of the invention has numerous advantages. Also, the composition of the invention may remove calcium ions. This is particularly advantageous in the case of plaque which sometimes contains ions such as calcium. Plaque may be difficult to remove by mechanical cleaning only. However, by removing calcium ions, the plaque disintegrates and may be removed with the conditioning composition. As the composition of the invention has a high pH, as mentioned above, it is possible to dissolve more EDTA therein, so that the final concentration of EDTA actually dissolved in the composition will be high compared to prior art compositions. The high amount of EDTA dissolved in the composition may be one reason for the composition's high efficiency in conditioning. The conditioning composition according to the present invention leaves a "clean" surface which facilitates attachment and re-growth of soft tissue to the mineralized surface or the implant. For example, tooth attachment may be improved by conditioning of a tooth root surface using the composition of the invention. In addition, the composition of the invention may be used for root canal conditioning e.g. in order to remove pulp tissue. The conditioning also leads to a reduced risk for inflammation and/or infection as e.g. bacteria, bacterial toxin and/or infected/necrotised tissue is removed from the mineralized surface and/or implant surface. In addition, the conditioning of a mineralized surface and/or implant surface using the composition of the invention also has the effect of increasing the hydrophilicity of the surface. This may also lead to accelerated bone and soft tissue re-growth. In addition, the conditioning of a surface with the composition of the invention may improve the bonding of restorative dental materials such as amalgams, composites, resins and cementitious materials. The composition of the invention may therefore be used for one or more of the above stated purposes. What is more, the composition of the invention is non-toxic.

The composition of the invention is particularly useful for the prevention and/or treatment of different disease and/or conditions in the oral cavity. Examples of such conditions include, but are not limited to, periodontal disease, periimplantitis, caries and/or an infection and/or inflammation in the root canal. The invention is thus also directed to the conditioning composition for use as a medicament. The invention is in addition directed to the conditioning composition for use in the prevention and/or treatment of a periodontal disease, periimplantitis, caries and/or an infection and/or inflammation in the root canal. Such a prevention and/or treatment comprise the conditioning of a mineralized dental surface and/or the surface of a dental implant with the composition of the invention. In such a prevention and/or treatment the mineralized surface and/or the implant surface may benefit from the prevention and/or treatment, but also surrounding soft tissue may benefit, as the removal of infectious bacteria, toxins, necrotized tissue etc. also e.g. may cause a soft tissue inflammation and/or infection to heal. For example, in the prevention and/or treatment of periodontal disease one or more of the affected tissues, including the gums, periodontal ligament, cementum, and alveolar bone may react positively to the prevention and/or treatment.

Periimplantitis is an inflammation in and around the area of a dental implant that may also affect abutment areas. By the use of the composition of the invention for the conditioning of the surfaces of a dental implant, and/or the bone to which the implant is attached, the treatment outcome of the periimplantitis may be improved as e.g. infectious material and/or necrotized tissue may be removed by using a composition of the invention. Also, conditioning of an implant surface with the composition of the invention may enable and/or enhance the osseointegration of the implant. The composition of the invention may therefore be used for enhancing and/or enabling the osseointegration of an implant. The invention is thereby also directed to a method for enabling and/or enhancing the osseointegration of an implant comprising treating the implant with a conditioning composition of the invention. The composition of the invention is particularly interesting for use in the prevention and/or treatment of periimplantitis.

As mentioned above, the composition of the invention may also be beneficial in the case of an infection and/or inflammation in a root canal. Pulpitis is an example of an inflammation in the root canal that may be caused by dental caries. Pulpitis causes increased sensitivity to stimuli, such as heat and cold. In such a prevention and/or treatment of an infection and/or inflammation in a root canal, dead and/or infected tissue, including any bacteria, is removed by conditioning with the composition as defined herein, optionally in combination with mechanical cleaning of the root canal.

Another embodiment the invention resides in a composition for use in tooth root conditioning by selective removal of an exposed tooth root surface so as to improve subsequent attachment of the tooth in conjunction with periodontal surgery.

The invention is also directed to the use of a composition as defined herein for the preparation of a medicament for the prevention and/or treatment of a periodontal disease, periimplantitis, caries and/or an infection and/or inflammation in the root canal. The invention is also directed to a method for preventing and/or treating a periodontal disease, periimplantitis, caries and/or an infection and/or inflammation in the root canal comprising the administration of a therapeutically effective amount of a composition as defined herein to a subject, such as a mammal, in need thereof. Such prevention and/or treatment comprises the conditioning of a mineralized dental surface and/or the surface of a dental implant with the composition of the invention. The composition of the invention is particularly interesting in connection with the prevention and/or treatment of periimplantitis.

The invention also encompasses a method for the conditioning of a mineralized dental surface and/or a surface of a dental implant comprising treating the surface with an effective amount of the conditioning composition.

When the composition of the invention is used to condition a surface, such a method for conditioning comprises the steps of applying the composition to the surface to be treated, allowing the composition to act for a suitable time period, and thereafter removing the composition from the surface, preferably by rinsing with water or a physiological salt buffer. After application of the composition to the surface to be conditioned in a manner suitable depending on the specific surface, the composition is allowed to act for a time period of typically a few minutes, such as 1, 2, 3, 4, 5, 6, 7 or 8 minutes. Preferably, the composition is applied for 5 min or less. Due to the high pH of the composition and the high amount of dissolved, i.e. available, EDTA, such short treatment times are possible.

Even if the composition of the invention is a powerful conditioning agent, the composition is mainly applied to a "dead" surface or a surface where without treatment nothing would grow. Thereby the risk that tissue is negatively affected by the composition is reduced. Also, the viscosity increasing agent that preferably is added to the composition allows for the composition to be applied to and basically stay at its site of application, thereby also reducing the risk for negative effects on tissue. After being allowed to act on a surface, the composition is removed from the surface, e.g. by rinsing with sterile water or water for injection or a physiological buffer, such as 0.9% NaCl. The rinsing is preferably performed until no more of the conditioning composition is visible on the surface. The composition may be applied by the use of any device suitable for the specific surface the composition is to be applied to. One example of such a device is a syringe, which may be used e.g. in the case of application to a root canal surface or other narrow or confined space. The composition may also be applied to a sponge, compress and the like, which then is used to clean the surface. Alternatively, the composition may be used in conjunction with different cleaning devices such as conventional brushes intended for the cleaning of a mineralized surface and/or implant surface. The invention thus is also directed to a kit comprising a vial with the conditioning composition and a device for the application to, and/or a device for cleaning, a mineralized dental surface and/or a surface of a dental implant. One example of such device is the device disclosed in WO2009083281. Alternatively, the composition may be provided directly in a device intended for application of the composition to a surface. Such a device may also be intended for storage of the composition before use. The kit may also comprise instructions for the cleaning of surfaces using the kit of the invention and/or solutions, such as water or a physiological salt buffer, for removing the composition of the invention from the surface it has been applied to.

The composition of the invention is prepared by dissolving an amount of EDTA in water so that the final concentration is as defined herein and adjusting the pH with a suitable base (i.e. a pH buffering agent) to the desirable pH. The method for preparing the composition of the invention may also comprise the step of adding a viscosity increasing agent as defined herein to the composition to provide a final concentration as defined herein, either before, after or simultaneously with adding the EDTA. The pH of the composition may be adjusted before or after the addition of the EDTA and the optionally added viscosity increasing agent.

EXPERIMENTAL SECTION

Example 1

2.75 g CMC (Blanose) was slowly added to 70 g of water for injection. To avoid lumping, the water was heavily stirred.

After adding all CMC, the solution was heated up to 80° C. and the solution was stirred for an additional 20 min (max.) CMC should now be completely dissolved. The solution was cooled down to ca. 50° C. and 24 g of EDTA was slowly added to the solution. The pH was adjusted with 5 M NaOH to reach approximately pH 7. After 1 h, the solution was adjusted to 100 g. After additional 30 min of stirring, the solution was steam sterilized for 20 min at 121° C. After steam sterilization, the solution was stirred during the cool down phase.

Example 2

The 6.03 g of the solution (example 1) was taken and the pH was adjusted with 92.5 mg NaOH (100%). The pH was 8. Another solution was prepared with 5.98 g and the addition of 188.6 mg NaOH (100%). The pH of this solution was 9.

The appearance of all three solutions was different:
Solution 1 (pH 7): opaque
Solution 2 (pH 8): slightly opaque
Solution 3 (pH 9): transparent Example 3

The three solutions from example 3 were applied onto sand blasted and acid etched titanium discs. Approximately 0.6 ml of the solutions were applied on 3 discs each. After 2 mins, the solution was washed away with purified water. Until the measurement, the discs were kept in purified water. Prior to the determination of the contact angle, the samples were dried with argon. The contact angle was determined once per disc and the following values were found (see also FIG. 1):

TABLE 1 contact angles of titanium discs after treatment with EDTA compositions with different pH.

| Treatment | Contact angle |
| --- | --- |
| Titanium disc untreated | 122 |
| Titanium disc treated with EDTA solution (pH 7) | 72 |
| Titanium disc treated with EDTA solution (pH 8) | 85 |
| Titanium disc treated with EDTA solution (pH 9) | 41 |

The lower the contact angle of a surface is, the higher the hydrophilicity of the surface is. As can be seen, when a surface is treated with a composition having a pH of 9, the contact angle is decrease compared to when a lower pH is used. The use of such a composition therefore has the effect of increasing the hydrophilicity of the surface. The composition of the invention may therefore also have an improved conditioning effect.

The invention claimed is:

1. A conditioning composition comprising ethylenediaminetetraacetic acid (EDTA) at a concentration in the range of 21-55% by weight and having a pH from about 9.0 to about 11.5, wherein the conditioning composition increases the hydrophilicity of a metal-containing surface of a dental implant in an oral cavity, and wherein the conditioning composition is transparent.

2. A conditioning composition according to claim 1, wherein the concentration of EDTA is in the range of 21-27% by weight.

3. A conditioning composition according to claim 2, wherein the concentration of EDTA is in the range of 21.6-26.4% by weight.

4. A conditioning composition according to claim 1, wherein the pH is 9.0-10.5.

5. A conditioning composition according to claim 1, wherein the pH is 9.0-10.0.

6. A conditioning composition according to claim 1, further comprising a viscosity increasing agent.

7. A conditioning composition according to claim 6, wherein said viscosity increasing agent is selected from the group consisting of polysaccharides, proteins, glycoproteins and synthetic polymers.

8. A conditioning composition according to claim 6, wherein said viscosity increasing agent is selected from the group consisting of celluloses and derivatives and/or salts thereof, starches and derivatives and/or salts thereof, plant gums, capsular microbial polysaccharides, and algal polysaccharides.

9. A conditioning composition according to claim 6, wherein said viscosity increasing agent is carboxymethylcellulose, or a salt thereof.

10. A conditioning composition according to claim 1, wherein the composition is a medicament.

11. A conditioning composition consisting essentially of EDTA at a concentration in the range of 21-55% by weight, a pH buffering agent, and an aqueous solvent, said composition having a pH from about 9.0 to about 11.5, wherein the conditioning composition increases the hydrophilicity of a metal-containing surface of a dental implant in an oral cavity, and wherein the conditioning composition is transparent.

12. A conditioning composition consisting essentially of EDTA at a concentration in the range of 21-55% by weight, a pH buffering agent, an aqueous solvent and a viscosity increasing agent, said composition having a pH from about 9.0 to about 11.5, wherein the conditioning composition increases the hydrophilicity of a metal-containing surface of a dental implant in an oral cavity, and wherein the conditioning composition is transparent.

13. A method for preventing and/or treating a periodontal disease, periimplantitis, caries and/or an infection and/or inflammation in the root canal comprising the administration of a therapeutically effective amount of the conditioning composition according to claim 1 to a subject in need thereof.

14. A method according to claim 13, wherein said treatment comprises the conditioning of a mineralized dental surface and/or the surface of a dental implant with the conditioning composition.

15. A method according to claim 13, wherein the subject is a mammal.

16. A method for conditioning of a mineralized dental surface and/or a surface of a dental implant comprising treating the surface with an effective amount of the conditioning composition according to claim 1.

17. A method for enabling and/or enhancing osseointegration of an implant comprising treating the implant with the conditioning composition according to claim 1.

18. A kit comprising a vial with the conditioning composition according to claim 1 and a device for the application to, and/or a device for cleaning a surface of a dental implant.

* * * * *

UNITED STATES PATENT AND TRADEMARK OFFICE
CERTIFICATE OF CORRECTION

PATENT NO. : 9,925,397 B2
APPLICATION NO. : 13/114687
DATED : March 27, 2018
INVENTOR(S) : Daniel Fehr It is certified that error appears in the above-identified patent and that said Letters Patent is hereby corrected as shown below:

In the Drawings

Please replace Fig. 1 with Fig. 1 as shown on the attached page.

Signed and Sealed this
Thirtieth Day of October, 2018

Andrei Iancu
*Director of the United States Patent and Trademark Office*